US006007985A

United States Patent [19]
Warren

[11] Patent Number: 6,007,985
[45] Date of Patent: Dec. 28, 1999

[54] MACROMOLECULE DELIVERY METHOD AND COMPOSITION

[75] Inventor: Stephen L. Warren, Orange, Conn.

[73] Assignee: Yale University, New Haven, Conn.

[21] Appl. No.: 08/348,718

[22] Filed: Dec. 2, 1994

Related U.S. Application Data

[63] Continuation-in-part of application No. 08/089,991, Jul. 8, 1993, abandoned, which is a continuation-in-part of application No. 07/955,338, Oct. 1, 1992, abandoned.

[51] Int. Cl.$^6$ .................................................. C12Q 1/68
[52] U.S. Cl. .............................. 435/6; 536/24.5; 514/44
[58] Field of Search .................................. 435/6, 174, 5; 514/2, 44; 536/24.5; 530/388.1

[56] References Cited

PUBLICATIONS

Lee et al. PNAS 86: 3624–3628,1989.
James, Antiviral Chemistry and Chemotherapy, 2(4) 191–214, 1991.
Gura, Science 270:575577, 1995.
Corden Trends in Biochemical Science 15: 383–387, 1990.
Jackson et al. EMBO 12: 1059–1065, 1993.
Lassner et al. Molecular Biology 17: 229–234 (Of Interest), 1991.
Talmadge Advanced Drug Delivery Rev, 10:247–299, 1993.
Bregman, David G., et al., "Cytostellin distributes to nuclear regions enriched with splicing factors," *J. Cell Science* 107:387–396 (1994).
Warren, Stephen L., et al., "Cytostellin: A Nuclear Protein That Redistributes to Peripheral Cytoskeletal Locations During Mitosis and G1," *The Cell Cycle: Regulators, Targets and Clinical Applications* Chapter 29, pp. 211–221 (V.W. Hu, editor, Plenum Press, New York) (1994).
Baron et al., "Localization of the Centrin–Related 165, 000–M$_r$ Protein of PtK$_2$ Cells During the Cell Cycle," *Cell Motil. and the Cytoskel.* 18: 1–14 (1991).
Bennett and Davis, "Erythrocyte ankyrin: Immunoreactive analogues are associated with mitotic structures in cultured cells and with microtubules in brain," *Proc. Natl. Acad. Sci. USA.* 78: 7550–7554 (1981).
Corden, et al., *Trends Biochem. Sci.* 15:383–387 (1990)*.
Dahmus, M.E., "Phosphorylation of Eukaryotic DNA–dependent RNA Polymerase," *J. Biol. Chem.* 256:3332–3339 (1981).
Fakan, et al., "Localization and Characterization of Newly Synthesized Nuclear RNA in Isolated Rat Hepatocytes," *Exp. Cell. Res.* 99:155–164 (1976).
Fakan And Bernhard, "Localisation of Rapidly and Slowly Labelled Nuclear RNA as Visualized by High Resolution Autoradiography," *Exp. Cell Res.* 67:129–141 (1971).
Fakan and Puvion, "The Ultrastructural Visualization of Nucleolar and Extranucleolar RNA Synthesis and Distribution," *Int. Rev. Cytol.* 65:255–99 (1980).
Fakan and Nobis, "Ultrastructural Localization of Transcription Sites and of RNA Distribution During the Cell Cycle of Synchronized Cho Cells," *Exp. Cell Res.* 113:327–337 (1978).

Gerace et al., "Immunocytochemical Localization of the Major Polypeptides of the Nuclear Pore Complex–Lamina Fraction," *J. Cell Biol.* 79:546–566 (1978).
Henry, Sally M. and Lon D. Hodge, "Nuclear Matrix: A Cell–Cycle–Dependent Site of Increased Intranuclear Protein Phosphorylation," *Eur. J. Biochem.* 133:23–29 (1983).
Huang and Spector, "Nascent pre–mRNA transcripts are associated with nuclear regions enriched in splicing factors," *Genes and Dev.* 5:2288 (1991).
Jackson, et al., "Visualization of focal sites of transcription within human nuclei," *EMBO* 12:1059–1065 (1993).
Kramer, et al., "Monoclonal Antibody Directed Against RNA Polymerase II of *Drosophila melanogaster*," *Molec. Gen. Genet.* 180:193–199 (1980).
Laemmi, U.K., "Cleavage of Structural Proteins during the Assembly of the Head of Bacteriophage T4," *Nature.* 227:680–685 (1970).
Nickerson, Jeffrey A., et al., "A Normally Masked Nuclear Matrix Antigen That Appears at Mitosis on Cytoskeleton Filaments Adjoining Chromosomes, Centrioles, and Midbodies," *J. Cell. Biol.* 116:977–987 (1992).
O'Keefe, et al., Disruption of Pre–mRNA Splicing In Vivo Results in Reorganization of Splicing Factors, *J. Cell Biol.* 124:249–260 (1994).
Price and Pettijohn, "Redistribution of the Nuclear Mitotic Apparatus Protein (NuMA) during Mitosis and Nuclear Assembly," *Exp. Cell Res.* 166:295–311 (1986).
Smith et al., "Alterations in Chromatic Conformation Are Accompanied by Reorganization of Nonchromatin Domains That Contain U–snRNP Protein p28 and Nuclear Protein p107," *J. Cell Biol.* 101:560–567 [1985].
Spector, "Higher order nuclear organization: Three–dimensional distribution of small nuclear ribonucleoprotein particles," *Proc. Natl. Acad. Sci.* 87:147–151 (1990).
Thibodeau, Alain and Michael Vincent, "Monoclonal Antibody CC–3 Recognizes Phosphoproteins in Interphase and Mitotic Cells," *Experimental Cell Research* 195:145–153 (1991).
Towbin et al., "Electrophoretic transfer of proteins from polyacrylamide gels to nitrocellulose sheets: Procedure and some applications," *Proc. Natl. Acad. Sci. USA.,* 76:4350–4354 (1979).

(List continued on next page.)

*Primary Examiner*—Scott W. Houtteman
*Attorney, Agent, or Firm*—Arnall Golden & Gregory, LLP

[57] ABSTRACT

Antibodies to the large subunit of DNA-dependent RNA polymerase II (Pol II LS) and methods of use thereof, including use as research tools and for the diagnosis of proliferative diseases such as cancer and the screening of anti-cancer therapies, and a method for delivering molecules to predetermined sites in the nucleus of a cell using a molecule containing the C-terminal domain of the Pol II LS protein. The anti-Pol II LS antibodies are highly specific for phosphorylated Pol II LS and bind to the C-terminal domain of the Pol II LS molecule in a phosphorylation-dependent manner.

9 Claims, 2 Drawing Sheets

OTHER PUBLICATIONS

Wansink, et al., "Fluorescent Labeling of Nascent RNA Reveals Transcription by RNA Polymerase II in Domains Scattered Throughout the Nucleus," *J. Cell. Biol.* 122:283–293 (1993).

Warren, Stephen, et al., "Cytostellin: a novel, highly conserved protein that undergoes continuous redistribution during the cell cycle," *J. Cell. Sci.* 103:381–388 (1992).

Warren and Nelson, "Nonmitogenic Morphoregulatory Action of $pp60^{v-src}$ on Multicellular Epithelial Structures," *Mol. Cell. Biol.* 7:1326–1337 (1987).

Xing and Lawrence, "Higher Level Organization of Individual Gene Transcription and RNA Splicing," *Science* 259:1326–1330 (1993).

Yang et al., "Nu–MA: An Unusually Long Coiled–Coil Related Protein in the Mammalian Nucleus," *J. Cell Biol.* 116:1303–1317 (1992).

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 7 amino acids
      (B) TYPE: amino acid
      (D) TOPOLOGY: linear    (xi) SEQUENCE DESCRIPTION: SEQ ID NO:1:

Tyr Ser Pro Thr Ser Pro Ser
1              5

(2) INFORMATION FOR SEQ ID NO:2:

(i) SEQUENCE CHARACTERISTICS:
      (A) LENGTH: 7 amino acids
      (B) TYPE: amino acid
      (D) TOPOLOGY: linear    (xi) SEQUENCE DESCRIPTION: SEQ ID NO:2:

Tyr Ser Pro Thr Ser Pro Ala
1              5

(2) INFORMATION FOR SEQ ID NO:3:

(i) SEQUENCE CHARACTERISTICS:
      (A) LENGTH: 7 amino acids

```
            (B) TYPE: amino acid
            (D) TOPOLOGY: linear (xi) SEQUENCE DESCRIPTION: SEQ ID NO:3:

Tyr Ser Pro Thr Ser Pro Gly
1               5
```

MACROMOLECULE DELIVERY METHOD AND COMPOSITION

CROSS-REFERENCE TO RELATED APPLICATIONS

This is a continuation-in-part of U.S. patent application Ser. No. 08/089,991, filed Jul. 8, 1993, by Stephen L. Warren and Stuart D. Flynn, now abandoned, which is a continuation-in-part of U.S. patent application Ser. No. 07/955,338, filed Oct. 1, 1992, by Stephen L. Warren and Stuart D. Flynn, now abandoned.

The United States government has rights in this invention by virtue of National Cancer Institute Grant No. K08 CAO1339 and March of Dimes Birth Defects Foundation Grant No. 5-91-0647.

BACKGROUND OF THE INVENTION

This relates to the fields of immunology and protein biochemistry and more particularly relates to RNA polymerase II.

Cell Division

Eukaryotic cell division is achieved by a highly ordered sequence of events. Chromosomal DNA is replicated, condensed and then segregated by mitotic spindle apparatus. These events are repeated each time a cell divides. Interphase is the time interval through which non-dividing cells pass, and includes the first growth phase (G1), the DNA replication (or synthesis) phase (S), and the second growth phase (G2). The position of a cell within the G1-S-G2 sequence is usually determined biochemically by methods measuring DNA content or synthesis.

Upon completing duplication of genetic and nongenetic material, a cell undergoes mitosis, a complex process by which a cell separates into two daughter cells. Mitosis is divided into several stages including prophase, prometaphase, metaphase, anaphase, telophase and cytokinesis. These stages are usually defined by morphological criteria, such as chromosome condensation, nuclear disassembly, chromatid segregation, nuclear reassembly and cytokinesis (cell fission).

During prophase, the nuclear envelope disassembles and a marked reorganization of cytoplasmic and subcortical cytoskeletal structures begins. The transition from metaphase to anaphase is characterized by separation of the daughter cell chromatids, and the appearance of a cleavage furrow in the plane of the metaphase plate. Telophase cells are readily identified by their elongation in a direction perpendicular to the metaphase plate, reassembly of the nuclear lamina and envelope and a more prominent cleavage furrow. Cytoplasmic fission at the midbody results in partitioning of nuclear components, cytoplasmic membranes, associated cytoskeletal structures, organelles, and soluble proteins between the daughter cells.

Currently, cell cycle analysis is conducted indirectly by measuring an increase in DNA synthesis or content in a cell. For example, scientists measure the uptake of tritiated thymidine or the uptake of 5-bromo deoxyuridine by the cell. An increase in the concentration of either of these chemicals in the cell indicates that DNA synthesis is occurring. Alternatively, scientists use dyes that bind to DNA, such as propidium iodide, as an indication of DNA content. These methods are based upon DNA synthesis and content, and do not directly measure the number of cells in mitosis. Thus, mitotic activity, also referred to as the mitotic index, is presently determined indirectly.

RNA Polymerases

RNA polymerases are enzymes that synthesize cellular RNA from a DNA or RNA template. RNA synthesized by an RNA polymerase is complementary to its template. Cellular RNA polymerases take their instructions from DNA and are termed DNA-dependent polymerases. The nucleus of eukaryotes contains three types of RNA polymerases. RNA polymerase I (Pol I) is located in nucleoli and transcribes the genes for 18S, 5.8S, and 28S ribosomal RNA (rRNA). RNA polymerase III is located in the nucleoplasm and synthesizes the 5S rRNA molecule and the transfer RNA molecules (tRNA).

RNA polymerase II (Pol II) transcribes all protein-encoding genes. The largest subunit of Pol II (Pol II LS) has a molecular weight of approximately 240 kDa and is highly conserved in eukaryotic cells from yeast to humans. The second largest subunit of Pol II has a molecular weight of approximately 140 kDa. Antibodies to some RNA polymerases are available. For example, the antibody 8WG16, used for in vitro transcription studies, is available from Promega Corp. (Madison, Wis.) and the antibody ARNA3 is available from Cymbus Bioscience Ltd. (Chilworth Res. Ctr., United Kingdom). However, these antibodies have a low specificity for Pol II LS, are unable to bind to Pol II LS in paraffin sections, and fail to bind to Pol II LS from all eukaryotic cells.

Pol II synthesizes several small RNA molecules and also synthesizes the precursors of messenger RNA (mRNA). These RNA polymerase II transcripts (pre-mRNAs) are co-transcriptionally spliced and packaged into ribonucleoprotein (RNP) particles. The splicing of mRNA precursors into mRNA molecules is performed by small nuclear ribonucleoprotein particles (snRNPs) in a spliceosome complex. The mechanisms by which the pre-mRNA processing molecules are recruited to the newly formed Pol II transcripts are uncertain. In mammalian cells, many proteins and snRNPs that participate in pre-mRNA splicing are concentrated in irregularly-shaped intranuclear regions termed "speckle domains". Most nuclei have 20–50 speckle domains, which can be visualized by immunofluorescence microscopy using antibodies directed against a subset of hnRNPs, snRNPs and non-snRNP splicing proteins of the SerArg (SR) family, such as spliceosome assembly factor (SC35). Nuclear speckle domains can also be visualized by fluorescent in situ hybridization (FISH) using oligonucleotide probes complementary to spliceosomal snRNAs. At the ultrastructural level, discrete structures termed "interchromatin granule clusters" (ICGCs) are highly enriched with SC35 and several other molecules localized in speckles by light microscopic techniques. Less prominent SC35 immunolabeling is present in structures termed "perichromatin fibrils" (PCFs), which form a latticework in the nucleoplasm surrounding the ICGCS. Some perichromatin fibrils are closely associated with the ICGCs, while others are separate from ICGCs. The intense SC35 labeling in the ICGCs, combined with the weak SC35 labeling in the surrounding perichromatin fibrils network, correlates well with light microscopic images of SC35-stained speckles, which appear to be partially interconnected and irregularly shaped.

Nuclear speckles (ICGCs) contain many proteins and RNPs known to participate directly in pre-mRNA splicing reactions, and it is likely that partially or fully assembled spliceosomes are located in these regions. Speckles (ICGCs) are also enriched with poly A+RNAS, however, several studies indicate that RNA polymerase II (Pol II)-mediated transcription and/or splicing take place outside of the ICGCs. First, electron microscopic studies have shown that the ICGCs are weakly labeled following [³H] uridine pulses (reviewed by Fakan and Puvion, *Int. Rev. Cytol.* 65: 255–99 (1980)). Second, the poly A⁺ RNA in these domains is very stable, suggesting that this metabolic pool of poly A⁺ RNA is separate from shorter-lived pre-mRNAs, which are exported to the cytoplasm or degraded. Third, several studies showed that Pol II transcription takes place in nuclear sites which are separate from the ICGCs. Electron microscopic studies showed that the nucleoplasm surrounding the ICGCs is labeled strongly and more rapidly than the ICGCs; in fact, labeling is most concentrated in the perichromatin fibrils (Fakan and Bernhard, *Exp. Cell Res.* 67: 129–141 (1971); Fakan, et al., *Exp. Cell Res.* 99: 155–164 (1976); Fakan and Nobis, *Exp. Cell Res.* 113: 327–337 (1978); Spector, *Proc. Natl. Acad. Sci. USA* 87: 147–151 (1990)). Recent studies using 5' bromouridine 5' triphosphate to label nascent Pol II transcripts revealed 100–500 discrete Pol II transcription foci that are widely distributed in the nucleus (Jackson, et al., *EMBO* 12: 1059–1065 (1993); Wansink, et al., *J. Cell Biol.* 122: 283–293 (1993)). These focal transcription sites are resistant to nucleolytic treatments which remove approximately 90% of the chromatin, indicating that Pol II-mediated transcription is associated with a solid phase nuclear structure (Jackson, et al., 1993). Furthermore, the transcription foci are separate from the regions most enriched with SC35 (i.e., ICGCs), although weaker SC35 labeling coincides with transcription foci (Wansink, et al., 1993). Fourth, while FISH has shown that nascent pre-mRNA transcripts of some genes appear immediately adjacent to the speckles, transcripts of other genes are clearly separate from the speckles (Huang and Spector, *Genes and Dev.* 5: 2288 (1991); Xing and Lawrence, *Science* 259: 1326–1330 (1993)). These studies indicate that Pol II transcription takes place in discrete intranuclear domains that can be distinguished from the speckles (ICGCs) by various light and electron microscopic techniques.

Gene Therapy

Gene therapy is the introduction into a cell of an entire replacement copy of a defective gene to treat human, animal and plant genetic disorders. The introduced gene, via genetic recombination, replaces the endogenous gene. This approach requires complex delivery systems to introduce the replacement gene into the cell, such as genetically engineered viruses, or viral vectors.

Gene therapy is being used on an experimental basis to treat well known genetic disorders of humans such as retinoblastoma and cystic fibrosis.

Gene therapy also includes the delivery of pharmaceutical agents to the sites of gene expression, whereby they may modify or inhibit one or more steps in the pathway leading to pre-mRNA biogenesis. According to this broader definition of gene therapy, antisense oligonucleotides, inhibitory ribozymes, proteins and other pharmaceutical agents are delivered precisely to the sites of gene expression.

Tumor Biology

Physicians often base a diagnosis of cancer on morphological alterations observed in a tissue biopsy or exfoliated cells. Once a tumor has been detected, it is common practice in surgical pathology to "grade" the tumor. Tumor grading provides an estimate of the aggressiveness or biological behavior of the tumor, and involves identification of morphological changes correlating tumor behavior. One parameter used for the grading of certain types of tumors, such as uterine leiomyosarcoma, neuroblastoma, breast carcinoma, and others, is the mitotic activity of the tumor. The mitotic activity, or mitotic index, provides an estimate of the growth rate of the tumor. The pathologist examines microscopic sections of the tumor, stained with conventional cell stains such as hematoxylin and eosin, and counts the number of mitotic figures per high powered field. This procedure can be tedious and is subject to errors related to inadequate sampling and misinterpretation.

Finally, mitotic index does not invariably correlate with malignant potential of cancer cells, or preneoplastic lesions. Some benign, "reactive" processes are characterized by a high mitotic index, and certain malignant processes have surprisingly low mitotic indices. Thus, the most consistent defect of malignant growth is the acquisition of abnormal cell cycle kinetics, which may not be reflected by an increased mitotic index. A major shortcoming of current diagnostic methods is that they cannot detect altered kinetics of the cell cycle. A marker of abnormal cycling kinetics is therefore needed to discriminate between non-neoplastic rapid growth states and malignant growth states.

Currently, the diagnosis of leukemic relapse depends upon a morphological analysis of bone marrow biopsies. This method depends upon the ability of a pathologist to visually identify through the microscope the malignant cells in a section of bone marrow or peripheral blood and is relatively insensitive. Diagnosis is not difficult in florid cases of relapse, but if only a few malignant cells exist in a sample containing millions of normal cells, the diagnosis may be missed and the patient may fail to receive appropriate treatment.

The human eye, even with the aid of a sophisticated microscope, cannot reliably scan millions of cells. Therefore, a method for staining dividing cells, and cells on the verge of dividing, would provide a sensitive test for the detection of leukemic cells in the peripheral blood. Normal blood does not contain dividing cells, or cells that are on the verge of dividing, commonly referred to as cells in G2/M, indicating that the cells are in transition from G2 to M. Therefore, a staining procedure that would be specific for dividing cells in the peripheral blood could be used to diagnose relapse of a leukemic patient undergoing chemotherapeutic treatment.

Flow Cytometry

A more sophisticated way to assess the growth regulation of cells in a clinical specimen is to perform cell cycle analysis using a flow cytometer. Flow cytometric analysis can be used to measure the percent of cells in G1, S and G2 phases, based upon the amount of DNA in the tumor cell nuclei. This method has been very useful for generating prognostically valuable clinical information, and may be used by the oncologist in selecting a treatment protocol for the cancer patient. Despite its usefulness, the method of flow cytometry has limitations.

The first set of limitations are technical and logistical. An analysis of whole cells requires that fresh tissue biopsies be separated into a single cell suspension prior to analysis by digestion with proteolytic enzymes. This step must be done in a specialized laboratory facility having appropriately trained personnel. Results may be compromised due to degradation of biopsy material during transit to the specialized laboratory. In addition, this procedure fails to distinguish tumor cells liberated by enzyme digestion from non-tumor cells derived from adjacent stroma or glandular tissue.

Cell cycle analysis of individual cell nuclei may be accomplished by extracting nuclei from fixed tissues that have been embedded in paraffin blocks, and staining the DNA with a fluorescent dye, such as propidium iodide. The distribution of G1, S and G2 phase nuclei are roughly determined by the relative fluorescence intensity of the individual nuclei passing through the flow cytometer. This approach has been beneficial in that it provides prognostically valuable information, such as the fraction of cells in G1 or G2/M or the presence of aneuploidy, but has significant limitations. First, the extraction, staining and flow cytometric analysis of nuclei is technically demanding. Second, some variation exists in the integration of DNA dye into the nucleus due to differences in chromatin density. In addition, the S-phase fraction of the cell population cannot be measured directly by flow cytometric analysis. Therefore, the S-phase fraction must be calculated using a sophisticated computer analysis involving complex mathematical algorithms.

A direct, accurate method for determining the position in the cell cycle of a particular cell or the number of cells undergoing mitosis, or a specific phase of interphase, at any one time, would be a useful tool for both research and clinical diagnostics. For example, such a method would facilitate the diagnosis, prognosis, and monitoring of a proliferative disease such as cancer.

Therefore, it is an object of the present invention to provide a direct method for determining the cell cycle stage of a particular cell that is inexpensive, rapid, simple to perform, reproducible and accurate.

It is a further object of the present invention to provide a diagnostic tool for detecting cellular abnormalities that reflect abnormal cell cycle regulation or kinetics that occur at the onset or relapse of proliferative disease or cellular abnormalities that reflect dysplasia or atypical hyperplasia.

It is a further object of the present invention to provide a method for screening drugs for the ability to repair cancer cells.

It is a further object of the present invention to provide a method for determining the effectiveness of an anti-proliferative agent in vivo and in vitro.

It is a further object of the present invention to provide antibodies highly specific for the RNA polymerase II large subunit.

It is a further object of the present invention to provide a therapeutic tool for the delivery of therapeutic agents to the cell nucleus, particularly to precise intranuclear sites of Polymerase II gene transcription and storage.

SUMMARY OF THE INVENTION

Antibodies to the large subunit of DNA-dependent RNA polymerase II (Pol II LS) and methods of use, such as detection of abnormal cell mitosis, are described herein. Also described is a method for delivering a macromolecule to the sites of RNA polymerase II-mediated transcription in the nucleus of a cell using an isolated or synthetic Pol II LS C-terminal domain molecule or derivatives thereof.

The anti-Pol II LS antibodies described herein are highly specific for phosphorylated Pol II LS and bind in a phosphorylation-dependent manner. The antibodies bind to the C-terminal domain of the Pol II LS molecule where phosphorylation occurs. Due to their high specificity, the anti-Pol II LS antibodies are able to bind to Pol II LS molecules in fixed cells, including paraffin sections. Furthermore, they are able to detect Pol II LS as it migrates throughout the nucleus and cytoplasm of the cell, particularly in the small nuclear ribonucleoprotein particles or organelles (snRPs) of the nucleus.

Preferably, the anti-Pol II LS antibodies are monoclonal antibodies. Most preferably, the anti-Pol II LS antibodies are the antibodies mAb H14 and mAb H5, produced by hybridomas deposited with the American Type Culture Collection (ATCC) as ATCC Designations HB 11727 and HB 11728, respectively. The mAB H5 binds specifically to the hyperphosphorylated C-terminal domain of the Pol II LS molecule having a molecular weight of approximately 240–250 kDa, whereas the monoclonal antibody H14 binds to Pol II LS proteins that are phosphorylated to various degrees as reflected by the molecular weights of approximately 210–240 kDa.

Anti-Pol II LS antibodies are useful as research tools for studying cell replication or in clinical diagnostic procedures for the identification of mitotic cells. The antibodies can be used to detect Pol II LS throughout the cell during each mitotic phase of the cell replication cycle. Anti-Pol II LS antibodies are also useful for distinguish normal cycling cells from malignant cells. Anti-Pol II LS antibodies are therefore useful in the diagnosis of a proliferative disease such as cancer, relapse of the cancer, or in determining the effectiveness of a particular therapy being used in the treatment of a proliferative disease. The antibodies are also useful for screening drugs for the ability to cause cancer cell repair.

The anti-Pol II LS antibodies described herein are useful for isolating Pol II LS protein, which may be useful therapeutically to deliver macromolecules such as oligonucleotides, particularly antisense oligonucleotides, ribozymes, particularly inhibitory ribozymes, proteins, and pharmaceutical agents to specific functional domains in the eukaryotic cell nucleus, particularly to the sites of gene expression, whereby they may modify or inhibit one or more steps in the pathway leading to pre-mRNA biogenesis. Using the antibodies described herein, it was discovered that the C-terminal domain of the Pol II LS protein is required for Pol II LS molecules to associate with the speckle domains for storage purposes and to migrate to Pol II transcription sites to effect transcription. By manipulating the C-terminal domain of the Pol II LS molecule, or a synthetic or truncated derivative of the C-terminal domain, its targeting properties can be predetermined. The Pol II LS C-terminal domain, or derivative is therefore useful for the delivery of molecules, attached to the C-terminal domain or C-terminal domain derivative by conventional means, to either the speckled domains or to the Pol II transcription sites. The preferred molecules are macromolecules such as oligonucleotides, ribozymes, proteins such as anti-transcriptional peptides, and classical pharmaceutical agents. By delivering these molecules directly to the site of transcription, therapeutic effects, such as gene therapy, may be facilitated.

BRIEF DESCRIPTION OF THE DRAWINGS

FIGS. 1A and 1C are negative controls.

FIG. 1B shows expression of Pol II LS in an uninduced, undifferentiated cell.

FIG. 1D shows decreased expression of Pol II LS following five days of induction with 5 mM hexamethylene-bis-acetamide (HMBA).

DETAILED DESCRIPTION OF THE INVENTION

Antibodies to the largest subunit of DNA-dependent RNA polymerase II (Pol II LS), methods of use thereof, and a method for delivering a molecule to a cell nucleus are provided.

DNA-dependent RNA polymerase II is the enzyme that catalyzes pre-mRNA synthesis in all eukaryotic organisms.

The large subunit of DNA-dependent RNA polymerase II (Pol II LS) has a molecular weight of between approximately 220 and 240 kDa, depending on the degree of phosphorylation.

Antibodies were originally generated against an unidentified protein, believed to be a novel protein, by immunizing mice with a cell extract containing a mixture of phosphotyrosine-containing proteins purified from Madin Darby Canine Kidney cells. Using the antibodies, the unidentified protein was localized in the small nuclear ribonucleoprotein particles or organelles (snRPs) of the nucleus. The unidentified protein was subsequently identified as Pol II LS. This discovery was surprising because it was believed by those skilled in the art that the Pol II LS protein was excluded from intranuclear snRP organelles. The antibodies were unexpectedly found to be highly specific for the Pol II LS in its phosphorylated form. The anti-Pol II LS antibodies described herein are not only highly specific for phosphorylated Pol II LS, but bind in a phosphorylation-dependent manner. It is believed that this occurs because the antibodies bind to the C-terminal domain of the Pol II LS molecule where phosphorylation occurs.

The anti-Pol II LS antibodies described herein can be distinguished from the commercially available anti-Pol II LS 8WG16 antibody (Promega Corp. Madison, Wis.) and the ARNA3 antibody (Cymbus Bioscience Ltd. Chilworth Res. Ctr., United Kingdom) in several ways. For example, the anti-Pol II LS antibodies described herein are more highly specific for Pol II LS than the 8WG16 or ARNA3 antibodies. The 8WG16 and ARNA3 antibodies bind not only to Pol II LS, but also many additional proteins in whole cell extracts, whereas the antibodies described herein bind exclusively to Pol II LS in whole cell extracts. In addition, the anti-Pol II LS antibodies described herein bind to the Pol II LS of all eukaryotic cells from human to yeast. For example the antibodies specifically immunoprecipitate and immunoblot a single ~210 kDa protein (Pol II LS) from extracts of S. pombe and S. cerevisiae. Therefore, the antibodies bind to an epitope or epitopes that are apparently present in all eukaryotic Pol II LS molecules. It is believed that the epitope recognized by the antibodies, particularly mAb H14, contains the highly repeated amino acid sequence YSPTSPS. Furthermore, the anti-Pol II LS antibodies described herein bind to Pol II LS protein in cell extracts, viable cells, and fixed cells, including paraffin sections.

The highly specific anti-Pol II LS antibodies are useful for detecting Pol II LS as it migrates throughout the nucleus and cytoplasm of the cell, and are particularly useful for detecting Pol II LS in the small nuclear ribonucleoprotein particles or organelles (snRPs) of the nucleus. No other antibodies seem to detect this subpopulation of Pol II, perhaps because their epitopes are "masked" in situ. Using the antibodies, Pol II LS was found to be continuously redistributed to multiple discrete sites throughout the cell during each mitotic phase of the cell replication cycle. In particular, when genes are activated, Pol II LS migrates from the snRP organelles to sites of gene expression. Therefore, the Pol II LS antibodies described herein can be used as research tools, such as for studying cell replication, or in clinical diagnostic procedures, such as for the identification of mitotic cells. For example, the antibodies are useful for marking the cell cycle stage in unsynchronized cell populations, in the diagnosis of a proliferative disease such as cancer or relapse of the disease, or in determining the effectiveness of a particular pharmacological drug or therapy being used in the treatment of a proliferative disease as discussed in more detail below.

In particular, the antibodies described herein have been used to detect an accumulation of Pol II LS in the extranuclear compartment of 75% of human breast cancers. It is believed that abnormal tyrosine phosphorylation of the C-terminal domain of Pol II LS causes this accumulation, which leads to aberrant intranuclear localization and function. Therefore, the detection of excessive extranuclear Pol II LS can be used to diagnose or monitor therapies used in the treatment of oncogenic diseases such as breast cancer.

Anti-Pol II LS antibodies are also useful for the isolation of purified Pol II LS. Isolated or recombinant derivatives of Pol II LS, due to its ability to undergo regulated shuttling between the nucleus and the cytoplasm, can be useful for delivering molecules, preferably macromolecules such as oligonucleotides, particularly antisense oligonucleotides, ribozymes, particularly inhibitory ribozymes, proteins, and pharmaceutical agents to specific functional domains in the eukaryotic cell nucleus, particularly to the sites of gene expression, whereby they may modify or inhibit one or more steps in the pathway leading to pre-mRNA biogenesis and be useful for therapeutic purposes such as gene therapy. Isolated or modified Pol II LS may also be useful for inhibiting or modifying transcription and splicing reactions.

Preferably, the anti-Pol II LS antibodies are monoclonal antibodies. Most preferably, the anti-Pol II LS antibodies are the antibodies mAb H14 and mAb H5, produced by hybridomas which have been deposited with the American Type Culture Collection (ATCC) as ATCC Designations HB 11727 and HB 11728, respectively. These hybridomas were received and accepted by the ATCC on Oct. 13, 1994 and were tested for viability and found to be viable on Oct. 19, 1994, in accordance with the Budapest Treaty. These monoclonal antibodies are referred to herein as monoclonal antibodies H5 and H14. The monoclonal antibody H5 (produced by the hybridoma designated HB 11728) binds to the hyperphosphorylated Pol II LS protein having a molecular weight of approximately 240–250 kDa, whereas the monoclonal antibody H14 (produced by the hybridoma designated HB 11727) binds to a Pol II LS protein that is phosphorylated to various degrees as reflected by apparent molecular weights between approximately 210 and 240 kDa. The most preferred monoclonal antibody is the monoclonal antibody H5 due to its unique specificity for the hyperphosphorylated Pol II LS protein.

Isolation of Pol II LS and Generation of Pol II LS Antibodies

A highly phosphorylated 240 kDa protein was isolated by immunizing mice with a cell extract containing a mixture of phosphotyrosine-containing proteins purified from Madin Darby Canine Kidney (MDCK) cells expressing elevated levels of the cellular tyrosine kinase pp60$^{C-SRC}$, a tyrosine-specific protein kinase cellular homologue of v-src encoded by the Rous sarcoma virus; fusing immunoreactive splenocytes to myeloma cells to produce hybridomas using standard techniques; screening the hybridoma for the ability to produce antibodies; and testing the antibodies for the ability to immunoprecipitate the 240 kDa protein as described in more detail below in the examples.

The 240 kDa protein was subsequently identified as the large subunit of DNA-dependent RNA polymerase II (Pol II LS) as described above.

It will be understood by those skilled in the art that similar monoclonal or polyclonal antibodies having the characteristics of the monoclonal antibodies H5 an dH14 could be prepared using the same or similar methods in combination with well-known routine antibody production techniques. In addition, antibodies could be generated against the purified Pol II LS protein isolated using the monoclonal antibodies H5 or H14 as described below.

Labelled Anti-Pol II LS Antibodies

Anti-Pol II LS antibodies can be directly or indirectly labelled with a detectable label to facilitate detection of the presence of the antibodies by detection of the label. Various types of labels and methods of labelling antibodies are well known to those skilled in the art. Several specific labels are set forth below.

For example, the antibody can be labelled directly or indirectly with a radiolabel such as, but not restricted to, $^{32}P$, $^{3}H$, $^{14}C$, $^{35}S$, $^{125}I$, or $^{131}I$. The radiolabel is generally attached by chemical modification. Detection of a label can be by methods such as scintillation counting, gamma ray spectrometry or autoradiography.

Fluorogens can also be used directly or indirectly to label the anti-Pol II LS antibodies. Examples of fluorogens include fluorescein and derivatives, phycoerythrin, allophycocyanin, phycocyanin, rhodamine, Texas Red or other proprietary fluorogens. The fluorogens are generally attached by chemical modification and can be detected by a fluorescence detector.

The anti-Pol II LS antibody can alternatively be labelled directly or indirectly with a chromogen to provide an enzyme or affinity label. For example, the antibody can be biotinylated so that it can be utilized in a biotin-avidin reaction which may also be coupled to a label such as an enzyme or fluorogen. For example the antibody can be labelled with peroxidase, alkaline phosphatase or other enzymes giving a chromogenic or fluorogenic reaction upon addition of substrate. Additives such as 5-amino-2,3-dihydro-1,4-phthalazinedione (also known as Luminol™) (Sigma Chemical Company, St. Louis, Mo.) and rate enhancers such as p-hydroxybiphenyl (also known as p-phenylphenol) (Sigma Chemical Company, St. Louis, Mo.) can be used to amplify enzymes such as horseradish peroxidase through a luminescent reaction; and luminogeneic or fluorogenic dioxetane derivatives of enzyme substrates can also be used. Such labels can be detected using enzyme-linked immunoassays (ELISA) or by detecting a color change with the aid of a spectrophotometer. In addition, antibodies may be labelled with colloidal gold for use in immunoelectron microscopy in accordance with methods well known to those skilled in the art.

The location of Pol II LS in cells can be determined by labelling the antibody as described above and detecting the label in accordance with methods well known to those skilled in the art. For example, the location of Pol II LS in cells can be determined by immunofluorescence microscopy using procedures such as those described by Warren and Nelson, *Mol. Cell. Biol.* 7: 1326–1337 (1987), and the anti-Pol II LS antibodies described herein.

Immunoaffinity Purification of Pol II LS

Pol II LS may be purified by standard immunoaffinity chromatography using one or a combination of the monoclonal antibodies described above covalently bound to agarose beads or bound non-covalently via a Goat-anti mouse IgM antibody to *Staphylococcus aureus* protein G beads (Sigma, Chemical Co., St. Louis, Mo.). Most preferably, Pol II LS is purified by affinity chromatography using the H5 monoclonal antibody.

Pol II LS isolation is achieved by incubating cell extracts, such as the MDCK cell extracts described above, with an anti-Pol II LS monoclonal antibody, such as the monoclonal antibody H5, attached to a solid phase, such as chemical conjugation to agarose beads. After incubation, the beads are washed, denatured and resolved on a polyacrylamide gel. Pol II LS purified from less than 50 mg of total MDCK cell protein is visible as a 240 kDa band stained with coommassie brilliant blue.

Pol II LS can be isolated from the cells and tissues of a wide variety of eukaryotic species as set forth below, thus facilitating biochemical and immunoaffinity purification.

As described above, purified Pol II LS protein is useful for polyclonal or monoclonal antibody production.

Evolutionary Conservation of Pol II LS

The antibodies described herein are specific for a highly conserved epitope of Pol II LS. The evolutionary conservation of Pol II LS was determined by solubilizing cell proteins from the cells and tissues of a wide variety of eukaryotic species including human (CACO2 colonic adenocarcinoma cell line), dog (Madin Darby Canine Kidney cell line), mouse (murine erythroleukemia stem cells), chicken, newt (*Triturius viridescens* tissue), fish (*Lesbistes reticularis* tissue), insect (*D. melanogaster*), nematode (*C. elegans*) and yeast (*S. pombe*). Solubilized proteins were separated on 7% SDS polyacrylamide gels as described by Laemmli, *Nature.* 227: 680–685 (1970), transferred to nitrocellulose membranes, and blotted with the monoclonal antibody H5.

Monoclonal antibody H5 binds to Pol II LS protein in all species tested from yeast to humans. The Pol II LS molecules in amphibian and fish have a molecular weight greater than 240 kDa, whereas the molecules in mammals, birds, insects and nematodes are approximately 240 kDa. The yeast protein is approximately 210 kDa. All of these eukaryotic homologues are detected by the anti-Pol II LS monoclonal antibody, H14. The data strongly suggest that H5 and H14 bind to separate epitopes on Pol II LS.

Research Applications for Pol II LS and Pol II LS Antibodies

Isolated Pol II LS and antibodies specific for Pol II LS can be used for cell cycle analysis of cells, such as cultured or harvested cells for various purposes including scientific research. As described above, anti-Pol II LS antibodies may be reacted with cells or cell nuclei, and bound antibodies detected by conventional methods well known to those skilled in the art. The specific location of the bound antibodies in extranuclear or intranuclear portions of the cell can be used to determine the location of Pol II LS in the cell which, in turn, can be used to mark the position of the cell in the cell cycle at a single point in time. The antibodies can therefore be used in any experiment which includes a cell cycle analysis of normal, cycling eukaryotic cells.

Pol II LS antibodies may be used to determine the fraction of cells in a population that are at each stage of the cell cycle. Pol II LS antibodies can, therefore, be used as a tool for cell cycle analysis that allows the analyst to make inferences regarding the kinetics of the cell cycle without performing kinetic-based experiments. Analysis can be conducted in conjunction with automated methods such as flow cytometry and image analysis.

In addition, human cancer cells stained with anti-Pol II LS antibodies show abnormal localization, implying abnormal cell cycle regulation. Normal non-mitotic cells contain little or no detectable Pol II LS in the cytoplasm. However, malignant non-mitotic cells display a marked increase in cytoplasmic Pol II LS immunoreactivity, indicating abnormal cell cycle regulation of the nucleoplasmic movement of Pol II LS. The movement is abnormal in that Pol II LS is retained in the cytoplasm after the completion of mitosis and does not return to the nucleus or it returns with delayed kinetics.

Clinical Diagnostic Applications for Pol II LS and anti-Pol II LS Antibodies

Anti-Pol II LS antibodies can be used to detect and distinguish proliferating cells from non-proliferating cells and to distinguish malignant non-dividing cells from normal non-dividing cells in a biological sample taken from a human patient or research animal. The biological sample can be a tissue biopsy, cells in a biological fluid such as a peripheral blood smear, and a cytological specimen such as a cervical smear. In addition, because the antibodies described herein stain both fresh tissues and tissues fixed in formalin and embedded in paraffin, the biological sample can be fresh or preserved. Therefore, anti-Pol II LS antibodies can be used as diagnostic agents for the diagnosis of a proliferative disease such as cancer, relapse of a proliferative disease such as neoplasia, or to assess the effectiveness of a particular therapy, such as chemotherapy or radiation therapy for treatment of a proliferative disease. In particular, anti-Pol II LS antibodies can be used for early diagnosis of rapidly dividing tumors, such as seminoma and acute leukemia. Furthermore, anti-Pol II LS antibodies can be used for endometrial dating to allow an easy, quick assessment of a proliferative endometrial cell sample exfoliated from the endometrial lining of the uterus and for analysis of early "precursor" lesions, such as atypical hyperplasias or fibrocystic changes in breast tissue biopsies, or atypical hyperplasia of the endometrial glands for identification of those individuals at greatest risk for the development of cancer.

Human cancer cells consistently show abnormalities in Pol II LS distribution or expression that allow an analyst to distinguish malignant cells from non-neoplastic cycling cells in tissue sections. An estimated 70% of cases show abnormal cytoplasmic distribution and many (10–15%) show a marked increase in the nuclear immunoreactivity of Pol II LS. Pol II LS appears to be retained, or trapped, in the cytoplasm of cancer cells, whereas in normal cycling cells Pol II LS returns to the nucleus after cell division. Furthermore, some rapidly growing cancers exhibit enhanced intranuclear Pol II LS immunoreactivity in addition to abnormal localization. Therefore, the anti-Pol II LS antibodies described herein enable a pathologist to identify, objectively and rapidly, malignant cells for a more accurate diagnosis of cancer.

Use of C-Terminal Domain for Macromolecular Delivery

Using the antibodies described herein, it was discovered that the C-terminal domain of the Pol II LS protein targets the Pol II LS molecule to the speckle domains of the nucleus for storage purposes and to Pol II transcription sites. The Pol II LS molecule having a hyperphosphorylated C-terminal domain associates with the speckle domains and transcription sites, whereas the Pol II LS molecule containing hypophosphorylated forms of the C-terminal domain are diffusely distributed in the nucleus and thus not attached to functional nuclear domains. By manipulating the C-terminal domain of Pol II LS, the migration of the Pol II LS molecule can be predetermined.

It has been discovered that the C-terminal domain acts in a dominant fashion to localize indicator proteins to discreet sites in the nucleus. Even after removing 80% of the non-C-terminal domain portion of the Pol II LS molecule by mutagenesis, the resulting construct maintained the ability to localize to the speckled domains or transcription sites in the nucleus. This indicates that the C-terminal domain functions as a localizing domain for RNA Polymerase II.

A Pol II LS C-terminal domain is defined herein as nucleotides 4760 to 5910 of the Pol II LS molecule, wherein nucleotide position number 1 is the adenylate residue of the ATG start codon of the Pol II LS molecule, and derivatives thereof. Pol II LS C-terminal domain derivatives are defined herein as molecules that include an isolated or synthetic molecule having an amino acid sequence and structure similar or identical to the C-terminal domain of the Pol II LS molecule. The C-terminal domain consists of 52 heptapeptide repeats similar or identical to the consensus sequence, Tyr-Ser-Pro-Thr-Ser-Pro-Ser (YSPTSPS), Sequence ID. NO: 1. It is believed that YSPTSPS, Sequence ID. NO: 1 or variant peptides such as YSPTSPA, Sequence ID. NO: 2, or YSPTSPG, Sequence ID. NO: 3, are competent to deliver molecules to sites of Pol II gene transcription. It is believed that the phosphorylation site of the C-terminal domain contains the highly repeated amino acid sequence YSPTSPS.

The Pol II LS C-terminal domain is useful, alone or in combination with the entire Pol II LS molecule, or portions thereof, for the delivery of molecules to either the speckled domains or sites of RNA Pol II-mediated transcription in the nucleus. The molecules to be delivered are attached to the C-terminal domain or C-terminal domain derivative by conventional means well known to those skilled in the art such as conjugation, expression of a fusion oligonucleotide, or oligonucleotide synthesis. The preferred molecules are macromolecules such as oligonucleotides, ribozymes, proteins, most preferably anti-transcriptional peptides, and pharmaceutical agents. By delivering these molecules directly to the site of transcription, therapeutic effects, such as gene therapy, may be facilitated.

For example, the C-terminal domain is useful therapeutically to deliver oligonucleotides, ribozymes, or proteins to the site of transcription by extending the synthetic sequence of the C-terminal domain to include the therapeutic sequence. In addition, a pharmaceutical compound, or other therapeutic chemical or pharmaceutical agent may be attached to the C-terminal domain by substituting one of the residues of the non-helical portion of the polypeptide, preferably a glycine or threonine residue, with an amino acid containing a free sulfhydryl such as cysteine, and then coupling the compound to the cysteine residue by a disulfide linkage. The compound is then transmitted to functional domains within the nucleus by the C-terminal domain. The site of delivery is predetermined by the C-terminal domain as described above. In addition, other chemical linkages known to those skilled in the art could be used to attach the compound to the polypeptide. The specificity of the C-terminal domain for a particular type of cell may be improved by attachment of a targeting molecule, such as an antibody or receptor molecule, to the polypeptide. A target protein molecule is attached by a peptide bond while a target chemical is attached by a sulfhydryl or disulfide bond as described above.

The C-terminal domain-molecule complex can be inserted into a unilamellar phospholipid vesicle or liposome for delivery to the cell requiring therapy. Liposomes are formed from commercially available phospholipids supplied by a variety of vendors including Avanti Polar Lipids, Inc. (Birmingham, Ala.). The liposome-associated polypeptide is prepared by mixing an aqueous solution of the polypeptide, prepared as described below, with reconstituted lipid vesicles. Preferably the lipid vesicles are reconstituted in a buffer solution containing approximately 20 mM sodium chloride and 5 mM sodium phosphate at an approximate pH of 8.0. The liposome can include a ligand molecule specific for a receptor on the surface of the target cell to direct the liposome to the target cell. If the C-terminal domain polypeptide is used for the delivery of a pharmaceutical compound to a cell, the lumen of the liposome preferably can contain additional compounds in solution for regeneration of uncoupled polypeptide.

Preferably, the C-terminal domain complex is dissolved in a physiologically-acceptable carrier, such as an aqueous solution or is incorporated within liposomes, and the carrier or liposomes are injected into the organism undergoing genetic manipulation, such as an animal requiring gene therapy. The preferred route of injection in mammals is intravenous. It will be understood by those skilled in the art that oligonucleotides are taken up by cells and tissues in animals such as mice without special delivery methods, vehicles or solutions.

For in vitro research studies, a solution containing the C-terminal domain complex is added directly to a solution containing the DNA molecules of interest in accordance with methods well known to those skilled in the art.

If the target gene contains a mutation that is the cause of a genetic disorder, then the C-terminal domain complexed with an oligonucleotide is useful for repair that may restore the DNA sequence of the target gene to normal. If the target gene is an oncogene causing unregulated proliferation, such as in a cancer cell, then the C-terminal domain complex is useful for deleting or mutating the target gene in order to terminate or reduce the uncontrolled proliferation of the cell. The C-terminal domain complex is also a useful anti-cancer agent for activating a repressor gene that has lost its ability to repress proliferation.

The C-terminal domain complex can also be used as a molecular biology research tool to cause recombination or inhibit the transcription of any gene for the study of mechanisms such as, for example, DNA repair.

The anti-Pol II antibodies and methods of use described above will be further understood with reference to the following non-limiting examples.

EXAMPLE 1

Production of H5 and H14 Monoclonal Antibodies and Identification of Specificity for Pol II LS The monoclonal antibodies H5 and H14 were produced and their specificity for Pol II LS was determined as follows.

Immunogen Preparation

MDCK cells were grown to confluence on Cytodex™ 3 microcarrier beads (Pharmacia Inc. , Piscataway, N.J.) in two liter spinner culture flasks. The cell-coated beads were washed three times with cold buffer (TBS buffer) containing 50 mM Tris-HCl pH 7.2, 150 mM NaCl, and 1 mM phenylmethylsulfonyl fluoride (PMSF), and then extracted for 15 minutes in an ice-cold "phosphotyrosine extraction buffer" containing 50 mM Tris-HCl pH 7.2, 150 mM NaCl, 0.5% TRITON X-100™ surfactant, 0.5% sodium deoxycholate, 1 mM PMSF, 2 mM $NaN_3$ and 0.2 mM $Na_3VO_4$. Insoluble material was pelleted by centrifugation at 20,000 ×g for 30 minutes. The clarified extract was passed twice over a 1 ml anti-phosphotyrosine affinity column in which 4 mg of monoclonal antibody Py20 were covalently bound to 1 ml of agarose gel (Py20-agarose; ICN Immunobiologicals, Lisle, Ill.). The column was washed with a cold phosphotyrosine wash buffer containing 50 mM Tris-HCl, pH 7.2, 150 mM NaCl, 0.1% TRITON X-100™ surfactant, 0.2 mM $Na_3VO_4$ and 1 mM phenylmethylsulfonyl fluoride and then eluted with 5 mM phosphotyrosine in the phosphotyrosine wash buffer.

Immunization

Approximately 50 micrograms of phosphotyrosine-containing MDCK cell protein was homogenized with complete Freund's adjuvant and injected intraperitoneally into female BALB/c mice in accordance with methods known to those skilled in the art. Three weeks later, secondary immunizations were performed similarly, except that incomplete Freund's adjuvant was used.

Assay for Anti-Pol II LS Antibodies

Sera from the mice was assayed for the presence of antibodies directed against MDCK cell proteins by immunoblot analysis five to seven days after secondary and tertiary immunizations as follows. Immune response was judged to be "positive" when mice produced antibodies directed at specific MDCK cell proteins on immunoblots. The antibodies reacted strongly with a 240 kDa protein.

MDCK cell protein was prepared by boiling MDCK cells in a hot SDS lysis buffer containing 1% SDS, 10 mM $Na_2HPO_4/NaH_2PO_4$, pH 7.2, 150 mM NaCl, 2 mM $NaN_3$, 0.2 mM $Na_3VO_4$, 5 mM EDTA, and 2 mM EGTA. The viscous material was sheared five times through a 23 Gauge needle and diluted with six volumes of TRITON X-100™ surfactant/DOC dilution buffer containing 10 mM $Na_2HPO_4/NaH_2PO_4$, pH 7.2, 150 mNM NaCl, 0.5% TRITON X-100™ surfactant, 0.5% sodium deoxycholate, 1 mM PMSF, 2 mM $NaN_3$, 0.2 mM $Na_3VO_4$, 5 mM EDTA and 2 mM EGTA. The diluted extracts contained 0.14% SDS. The protein extracts were run on a 7% polyacrylamide gel for immunoblot analysis.

Proteins separated on the 7% polyacrylamide curtain gel were transferred to nitrocellulose membranes overnight at 500 mA and immunoblots were performed using standard procedures as set forth by Towbin et al., *Proc. Natl. Sci. U.S.A.* 76: 4350–4354 (1979).

Pre-immune mouse serum had little or no reactivity, whereas multiple bands were visible in lanes incubated in immune sera, including a prominent band at approximately 240 kDa.

Hybridoma production

Immune splenocytes were fused with X63Ag8.653 myeloma cells using standard polyethylene glycol-mediated fusion methods, and plated into 96-well plates at limiting dilution in Hypoxanthine-Aminopterin-Thymidine (HAT) selection medium.

Hybridomas producing antibodies directed at MDCK cell proteins of the desired molecular weight were identified by the immunoblot analysis described by Towbin et al., *Proc. Natl. Acad. Sci. USA.*, 76: 4350–4354 (1979), performed in a 45-lane multiblot chamber (Immunetics, Cambridge, Mass.). The subclass of each monoclonal antibody was determined by enzyme-linked immunoassay (Mouse Hybridoma Subtyping Kit, Boehringer-Mannheim, Indianapolis, Ind.). Hybridoma ascites was generated using standard techniques as described by Harlow and Lane, *Antibodies: A Laboratory Manual.* Cold Spring Harbor Laboratory, Cold Spring Harbor, N.Y. (1988) which is incorporated herein by reference.

Two hybridoma fusions produced approximately 1500 hybridoma clones which were screened by immunoblot analysis. Two hybridomas (referred to herein as H5 and H14) produced IgM monoclonal antibodies that bind specifically to a 240 kDa protein band on the nitrocellulose membrane. The 240 kDa protein was also immunoprecipitated by monoclonal antibody H5. Monoclonal antibody H14 binds to the p240 kDa protein immunoprecipitated by H5, and H5 binds specifically to the 240 kDa protein immunoprecipitated by H14, indicating that these two monoclonal antibodies react to the same protein. An additional approximately 210 kDa band is present if the protein is immunoprecipitated before immunoblot analysis, and is absent in samples immediately denatured in sample buffer, suggesting that the protein band is a proteolytic breakdown product of p240.

The antibodies were detected indirectly, by reactivity with a labelled goat anti-mouse antibody, as described below.

Studies using mammalian cells showed that the monoclonal antibodies H5 and H14 immunostain nuclear speckles that are enriched with splicing proteins, and that they immunoblot a major protein species at ~240 kDa and a minor species at 210 kDa. This protein was also found to undergo distinctive changes in its subcellular distribution and immunoreactivity during the cell cycle. Based upon these properties, the 240 kDa protein was initially named "cytostellin," to describe the stellate pattern of immunoreactivity in mitotic cells. Cytostellin was found to be readily extracted from DNAse treated rat liver nuclei, and was immunopurified with mAb H5. In some experiments cytostellin was extracted by boiling in 1% SDS, diluted, and then immunoprecipitated with mAb H5 to yield a single 240 kDa band on polyacrylamide gel electrophoresis (PAGE). In other experiments cytostellin was extracted under non-denaturing conditions, yielding a complex with prominent bands that migrate at 240 kDa and 140 kDa on PAGE. The p240 and p140 bands were excised, digested with trypsin in situ and subjected to HPLC to resolve the resulting peptides. Amino acid sequences of three peptides derived from p240 were surprisingly found to exactly match residues 430–444, 919–927 and 1059–1074 of the largest subunit of murine RNA polymerase II. The amino acid sequence of a peptide derived from p140 matched exactly with residues 137–145 of the second largest subunit of RNA Polymerase II. Thus, cytostellin, which was thought to be a novel protein, was unexpectedly found to be the largest subunit of RNA polymerase II (Pol II LS).

To confirm that mAbs H5 and H14 recognize Pol II LS, separate aliquots of p240 immunoprecipitated with each antibody were immunoblotted with mAb H5, mAb H14, mAb MOPC 104 (control IgM) and a commercially available anti-Pol II LS mAb, 8WG16. MAbs H5 and H14 specifically immunoprecipitated the same 240 kDa protein, which is also recognized on immunoblots by the anti-Pol II LS mAb 8WG16. Pol II LS that was immunoprecipitated by 8WG16 also bound specifically to mAbs H5 and H14 on immunoblots. The control mAb H22 immunoprecipitated a ~180 kDa protein that is not recognized by mAbs H5, H14 or 8WG16, and the control, mAb MOPC 104, did not bind Pol II LS or the ~180 kDa protein.

MAb 8WG16 bound to Pol II LS, but also many additional proteins in whole cell extracts. In contrast, mAbs H5 and H14 bound exclusively to Pol II LS in whole cell extracts. Both of these mAbs bound a ~240 kDa band in whole cell extracts from all eukaryotes tested from human to *C. elegans* (Warren, et al., *J. Cell Sci.* 103: 381–388 (1992)), and they specifically immunoprecipitated and immunoblotted a single ~210 kDa protein (Pol II LS) from extracts of *S. pombe* and *S. cerevisiae*. Therefore, mAbs H5 and H14 bind to epitope(s) which are appall eukaryotic in all eukaryotic Pol II LS molecules. More importantly, mAbs H5 and H14 are more specific anti-Pol II LS antibodies than all commercially available reagents tested (mAb 8WG16 and mAb ARNA3).

EXAMPLE 2

Determination of Cellular Distribution of Pol II LS by Anti-Pol II LS Antibodies The location of Pol II LS in cells was determined by immunofluorescence microscopy using procedures described by Warren and Nelson, *Mol. Cell. Biol.* 7: 1326–1337 (1987), and the anti-Pol II LS monoclonal antibody H5, with minor modifications.

Cells were grown on glass coverslips, and fixed in 1.7% paraformaldehyde (weight/volume) in phosphate buffered saline (PBS) containing 10 mM $Na_2HPO_4/NaH_2PO_4$, pH 7.2, and 150 mM NaCl. The fixed cells were washed in PBS for 15 minutes and permeabilized with PBS containing 0.5% TRITON X-100™ surfactant and 2 mM $MgCl_2$ for 15 minutes at room temperature. Cells were incubated in monoclonal antibody H5 or control IgM (10 µg/ml) for 60 minutes at room temperature. The cells were washed extensively with PBS and then incubated in biotinylated goat anti-mouse IgM antibody for 60 minutes at room temperature. The cells were washed again with PBS and incubated with avidin-rhodamine or avidin-fluorescein. To visualize the state of chromosomal condensation, cells were incubated with the DNA binding fluor, 4',6-diamidino-2-phenylindole (DAPI) at 5 µg/ml as described by Baron et al., *Cell Motil. and the Cytoskel.* 18: 1–14 (1991). Following extensive PBS washes, the coverslips were mounted and viewed under oil immersion with the 63X objective of a MRC-600 confocal microscope (Bio-Rad Laboratories, Richmond, Calif.) equipped with epifluorescence illumination, and photographed on Ektachrome EES film (Eastman Kodak, Rochester, N.Y.).

Immunolocalization studies using the monoclonal antibody H5 reveal a diffuse pattern of immunoreactivity in the nucleus of MDCK cells. Control IgM showed low background fluorescence indicating the specificity of the H5 nuclear staining. The distribution of Pol II LS was striking in daughter cell pairs that were either in the process of cytokinesis or had separated almost completely. Daughter cell pairs were identified readily by their symmetry, and by the presence of multiple, discrete, immunoreactive clusters scattered throughout the cytoplasm.

During interphase, Pol II LS is located in nucleus. Pol II LS moves from the nucleus to discrete locations in the cytoplasm as mitosis progresses. Therefore, Pol II LS is intranuclear in non-dividing cells, migrates to the cytoplasm during mitosis, and forms extranuclear bodies in newly replicated daughter cells.

To characterize the subcellular localization of Pol II LS at each phase of the cell cycle, MDCK cells were subjected to immunofluorescence microscopy as described above. The state of chromosomal condensation, and the contours of the nuclear periphery revealed by DAPI staining indicate the phase of the cell cycle for each cell in a microscopic field. MDCK cells were photographed through one filter to reveal the chromosomal DNA and the same microscopic fields of cells were photographed through a second filter to reveal the pattern of Pol II LS immunofluorescence.

Pol II LS immunoreactivity in interphase nuclei is mostly diffuse staining with a variable degree of fine punctate staining. The punctate dots are separated from the nuclear periphery by a continuous, submembranous zone which appears to follow the contours of the nuclear envelope.

Early prophase is identified by an intense, beaded appearance of the DAPI-stained nuclei, which reflects the onset of chromosomal condensation. Coincident with this change, Pol II LS immunoreactivity intensifies and appears as intranuclear Pol II LS bodies. Close inspection of the immunofluorescent images reveal that Pol II LS forms a "shell" that coats each chromosome as it condenses. A subset of the intranuclear "bodies" are therefore actually folded, condensed chromosomes coated with Pol II LS. The outermost bodies are arranged in a line separated from the nuclear periphery by a continuous zone, which lacks discrete immunofluorescent bodies. Mid-prophase cells are identified by increasing condensation of the chromosomes and a loss of the smooth edges at the nuclear periphery indicating early nuclear envelope disassembly. Coincident with these changes, a few Pol II LS-containing bodies begin to appear in positions outside of the disassembling nucleus. By late prophase, multiple Pol II LS bodies are dispersed widely to various positions, many of which are remote from the chromosomes.

Pol II LS remains widely dispersed throughout the cell during metaphase and anaphase. While the chromosomes and spindle apparatus per se do not stain prominently with monoclonal antibody H5 during these phases, a perichromosomal "shell" comprised of Pol II LS immunoreactivity is visible. The pattern of the Pol II LS immunoreactivity in metaphase and anaphase cells is variable: most cells are studded with discrete bodies throughout, with some Pol II LS-bodies being smaller than others, and, in other cells, Pol II LS immunofluorescence appears almost homogeneous. Metaphase and anaphase cells with either of these two staining patterns contain a distinct group of Pol II LS bodies that are positioned in a ring-like structure which surrounds the mitotic spindle apparatus. The peri-spindle Pol II LS bodies are larger and more intensely immunoreactive than the more peripheral bodies.

Telophase cells appear to have a variable degree of nuclear reassembly as indicated by the contour of the nuclear periphery, which is well-defined in some telophase cells and poorly defined ("fuzzy") in others. The monoclonal antibody H5 stained nascent nuclei in early and late stages of reassembly in addition to the cytoplasmic bodies. The Pol II LS bodies were widely distributed throughout the cytoplasm, including the tips of cell processes, which are far removed from the nucleus. The number of Pol II LS bodies is reduced in telophase cells compared to metaphase and anaphase cells. Significantly, the cytoplasmic Pol II LS bodies are present in late telophase cells and appear even in many of the daughter cells that have completed cytokinesis. Monoclonal antibody H5 did not stain centrioles or the midbodies between separating daughter cells.

EXAMPLE 3

Use of Pol II LS Antibodies for Diagnosis of Leukemia

A sample of blood cells (several million cells) is collected from patients at risk for leukemic relapse. The cells are washed, briefly fixed, permeabilized, reacted with the anti-Pol II LS antibody H5 or H14, and then reacted with a fluorescent-labelled antibody that binds to the monoclonal antibody. The cells are then subjected to flow cytometric analysis, which can detect a small number of fluorescent (high Pol II LS, or Pol II LS-positive) cells among a large number of nonfluorescent (low Pol II LS, or Pol II LS-negative) cells. The presence of an abnormal number of Pol II LS-positive cells is indicative of leukemic relapse because normal peripheral nucleated blood cells totally lack detectable Pol II LS immunoreactivity. It is believed that the mAb H5 epitope is "masked" in normal nucleated blood cells in the periphery. Leukemic blasts have intense nuclear Pol II immunoreactivity as detected by mAb H5. The presence of Pol II LS immunoreactivity in nucleated blood cells therefore indicates that they are blasts, which should not exist outside the bone marrow.

EXAMPLE 4

Use of Anti-Pol II LS Antibodies to Determine the Growth Rate of Cells

The anti-Pol II LS monoclonal antibody H5 was used to stain the nuclei of fixed murine erythroleukemia cells, and the stained nuclei were analyzed by flow cytometric cell cycle analysis.

Figure 1A:
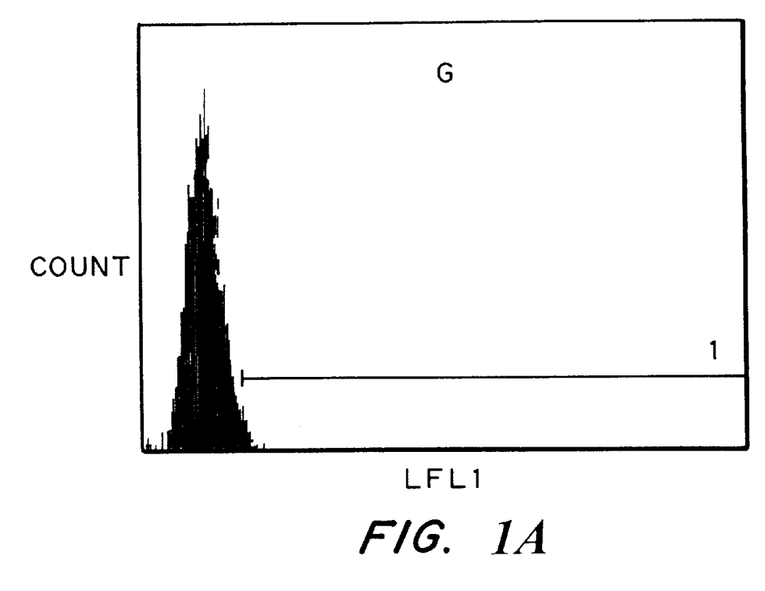
FIGS. 1A, 1B, 1C, and 1D are flow cytometry histograms showing expression of Pol II LS in murine erythroleukemia cells.
Figure 1B:
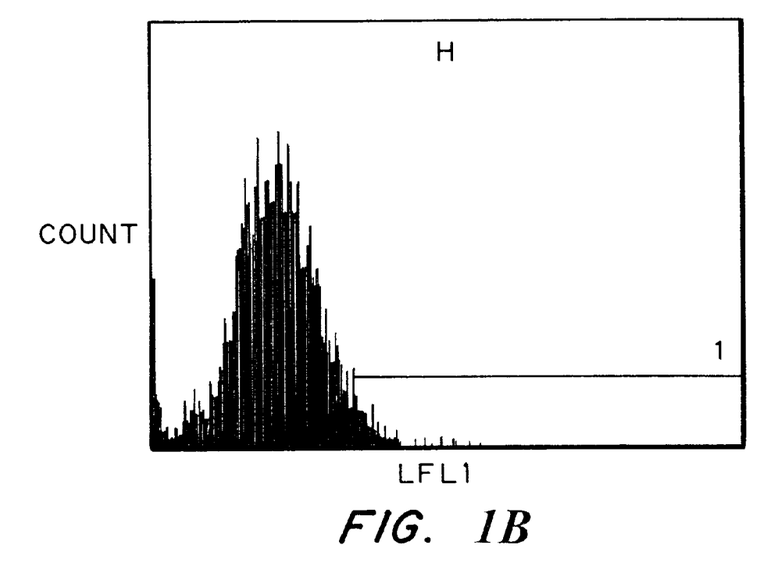
Figure 1C:
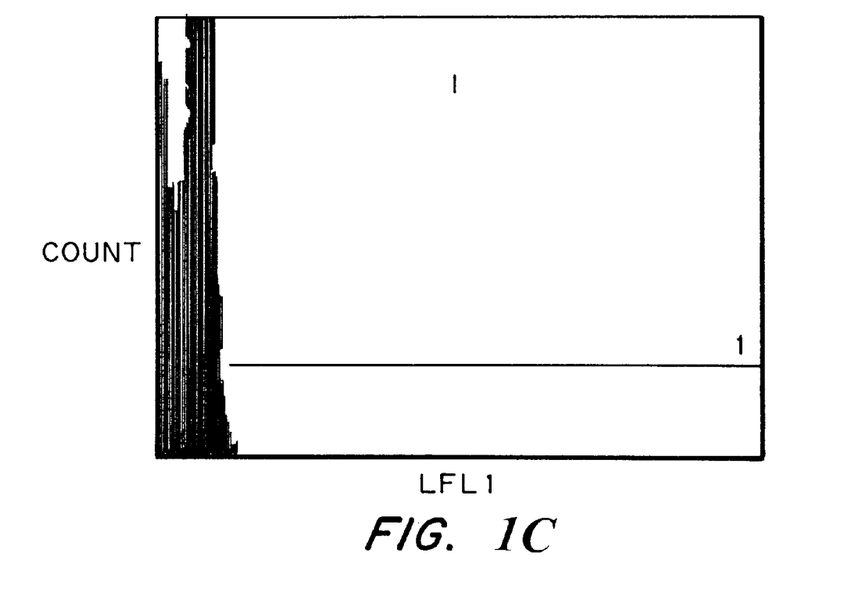
Figure 1D:
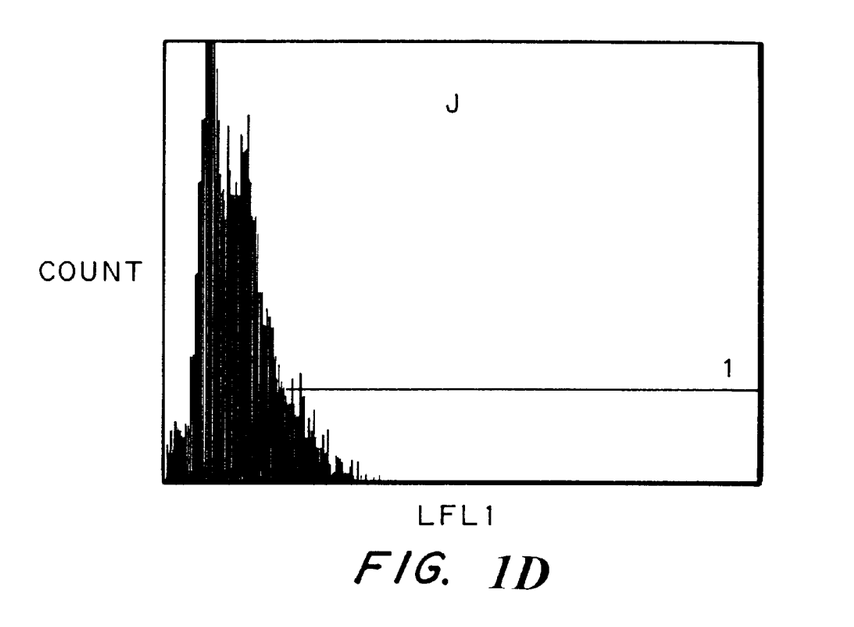

The results shown in FIGS. 1A–1D demonstrated that the percent of nuclei positively stained was directly proportional to the growth rate of the cells. This was done by determining the percent of monoclonal antibody H5-stained nuclei in a population of uninduced (rapidly growing) leukemic cells, shown in FIG. 1B, and in a population of induced (differentiating and slow growing) leukemic cells, shown in FIG. 1D. The antibody-stained nuclei of these two populations were readily distinguished.

These results demonstrate that anti-Pol II LS antibodies allow the generation of a "growth profile," that reflects the growth rate of fixed cells.

Example 5

Abnormal Subcellular Distribution of Pol II LS in Malignant Human Cells in vivo

Normal and malignant breast ductal cells were stained with the peroxidase-labelled anti-Pol II LS monoclonal antibody H5. Cytoplasmic Pol II LS was undetectable in normal, non-dividing breast ductal cells. However, in malignant, non-dividing ductal cells marked cytoplasmic Pol II LS immunoreactivity was observed. Similar results were obtained by immunoperoxidase staining of uterine leiomyosarcomas, germ cell neoplasms and other carcinomas. The abnormal nucleocytoplasmic compartmentalization of Pol II LS is a feature of many types of malignant cells.

EXAMPLE 6

Localization of Pol II LS in synchronized Cells

HeLa cells were synchronized using an initial aphidocolin block/release (S-phase block) followed by a nocodazole block/release (G2/M phase block). Nearly all of the cells were at G2/M following the nocodazole block, and they progressed relatively synchronously to S-phase, 10–12 hours later. Cells were synchronized effectively between S-phase and G2/M by reversing the sequence of the blocks; i.e. nocodazole block/release followed by aphidocolin block/release. All synchronizations were confirmed by flow cytometry.

Synchronized cells at each time point were analyzed by immunofluorescence microscopy using monoclonal antibody H5. Episodic intranuclear immunofluorescence first appears at the onset of G2/M.

Results indicated that Pol II LS does not undergo significant fluctuations during the cell cycle and that the phosphorylation state of the C-terminal domain of Pol II LS remains constant throughout the cell cycle as determined by mAb H % binding. Therefore, cell cycle dependent changes of H5 immunoreactivity (e.g. the episodic intranuclear immunofluorescence) indicate that changes occur in the conformation or organization of Pol II LS rather than the amount of Pol II LS.

EXAMPLE 7

Use of mAb HS to Detect Pol II LS and Pol II LS Subsets Under Various Conditions The monoclonal antibody H5 was used to detect Pol II LS within cells during various phases of cell division. A subpopulation of Pol II LS was found to be localized in nuclear speckle domains, tightly associated with a solid phase nuclear structure. This subpopulation was found to be hyperphosphorylated on the C-terminal domain.

Materials and Methods

Immunopurification of Pol II 240 and 140 kDa Subunits

The 240 kDa and 140 kDa subunits of RNA polymerase were immunopurified from the nuclei of 60 rat livers (700 g) utilizing a modification of the established nuclear fractionation procedure of Nickerson, et al., *Cell Biol.* 116: 977–987 (1992). Fresh minced livers were homogenized in a glass vessel with a rotating Teflon pestle in 10 ml/g liver ice cold CSK-100 buffered (100 mM NaCl, 0.3 M Sucrose, 3 mM $MgCl_2$. 10 mM Pipes pH 6.8, 1 mM EGTA, and 0.5% Triton X-100™ surfactant) to which was added 1 mM phenylmethyl sulfonyl fluoride (PMSF). The nuclei were collected by centrifugation at 200×g at 4° C., washed with several changes of CSK-100, and re-suspended in 1.5 ml/g liver of CSK-50 buffer (50 mM NaCl) and incubated with 110 μg/ml deoxyribonuclease (Sigma Chemical Co., St. Louis, Mo.) at 22° C. for 30 minutes then pelleted at 200×g. The nuclei were then extracted in either of two ways. To maximize the yield of the 240 kDa subunit, the nuclear pellet was re-suspended in 0.3 volumes of TBS (50 mM Tris-HCl 7.4, 150 mM NaCl, 1 mM PMSF) and then 3.3% SDS in TBS was added dropwise to a final concentration of 1% SDS. The suspension was heated in a boiling water bath for five minutes, passed repeatedly through a 19 gauge needle to shear chromosomal DNA, and then diluted with six volumes of ice cold Py20 lysis buffer (50 mM Tris HCl pH 7.4, 150 mM NaCl, 0.5% Triton X-100™ surfactant, 0.5% sodium deoxycholate, and 1 mM PMSF). To immunoprecipitate a complex of proteins including p240 and p140, the nuclear pellet was resuspended in ten volumes of TD buffer (50 mM Tris HCl pH 7.5, 0.5% Triton X-100™ surfactant, 0.5% sodium deoxycholate (DOC), 250 mM NaCl, 5 mM EDTA, 50 mM NaF, 1 mM PMSF, 1 mM sodium orthovanadate, 5 mM β-glycerophosphate). Insoluble material was removed by centrifugation at 16000×g at 4° C. for 20 minutes. Pol II was then immunoprecipitated with monoclonal antibody (mAb) H5 coupled to Protein G Sepharose 4 Fast Flow beads (Pharmacia, Piscataway, N.J.). Coupling was performed as follows: 50 μg of IgM mAb H5, 33 μg of rabbit anti-mouse IgM (Zymed, San Francisco, Calif.) and 66 μl of Protein G beads per rat liver were incubated in TBS for several hours at 4° C. The mAb H5-coupled beads were pelleted by centrifugation at 250×g and washed with TBS before being added to the 16000×g supernatant. Immunoprecipitation was performed by rocking end over end at 4° C. for 16 hours, the beads were washed three times with TD buffer, and the immunoprecipitated protein was eluted by incubating with 1.5 times the bead volume of sample buffer (3% SDS, 2 M urea, 62.5 M Tris HCl pH 6.9, 2 mM EDTA, and 3.5% (v/v) 2-mercaptoethanol) at 100° C. for five minutes. The beads were discarded and the eluate was lyophilized and re-suspended in 17 μl per rat liver of 62.5 mM Tris pH 6.8, 2 mM EDTA, 10% glycerol and 3.5% (v.v) 2-mercaptoethanol. The proteins were then resolved by 8% SDS-polyacrylamide gel electrophoresis (PAGE).

Cell Culture.

Madin Darby canine kidney (MDCK) cells were maintained in monolayer culture with Dulbecco's modified Eagle's medium (DME) supplemented with 7% fetal bovine serum. HeLa cells were maintained in monolayer culture with RPMI 1640 medium supplemented with 7% FBS and 10 mM glutamine (Gibco BRL, Gaithersburg, Md.). Where indicated the following transcriptional inhibitors (Sigma, St. Louis, Mo.) were added to the culture media at the indicated final concentrations and times: alpha amanitin (10 μg/ml, 8 hr); 5,6-dichlorobenzimidazole riboside (DRB, 100 μM, 3 hr); actinomycin D (20 μg/ml, 2 hr); N-(2[methylamino] ethyl)-5-isoquinolinesulfonamide (H8, 100 μM, 2 hr).

Immunoprecipitation and Immunoblotting.

MDCK protein extracts suitable for immunoprecipitation were prepared using hot "1% SDS lysis buffer" followed by dilution with "0.5% Triton X-100™ surfactant/0.5% deoxycholate dilution buffer" as described by Warren, et al., *J. Cell Sci.* 103: 381–388 (1992). Immunoprecipitations were performed using IgM mAbs H22, H14, and H5 coupled to protein G sepharose beads via a rabbit anti-mouse IgM linker antibody as described above. Whole cell extracts were obtained by scraping cells from nearly confluent culture dishes into hot 2× sample buffer and heating the sample to 100° C. for five minutes then shearing chromosomal DNA with a 19 gauge syringe. Immunoprecipitates as well as whole cell extracts were resolved by 8% SDS-PAGE and transferred to nitrocellulose as described by Towbin, et al., *Proc. Natl. Acad. Sci. USA.* 76: 4350–4354 (1979).

Immunofluorescence Microscopy.

Immunofluorescence microscopy and photography was performed using standard immunolocalization techniques essentially as described by Warren, et al., *J. Cell Sci.* 103: 381–388 (1992).

Alkaline Phosphatase Treatment.

Proteins immunoprecipitated with H14 coupled to protein G sepharose beads as described above were washed with 20 mM Hepes pH 7.3, 20 mM $MgCl_2$, 40 mM KCl, 0.2 mM PMSF as described by Rice, S. A., et al., *J. Virol.* 68: 988–1001 (1994). The immunoprecipitate was then exposed to calf intestine alkaline phosphatase (New England Biolabs, Beverly, Mass.) at a concentration of 500 units per ml in a volume of 75 μl (excluding bead volume) in the presence or absence of the phosphatase inhibitor beta glycerophosphate (5 mM) for five minutes at 37° C. The reaction was stopped and the proteins were eluted from the beads by adding 4× sample buffer and boiling for five minutes. The eluted proteins were analyzed by SDS-PAGE and Western immunoblot analysis as described above.

Fractionation of Pol II LS.

For Western immunoblot analysis, MDCK cells grown on 100 mm dishes were subjected to appropriate drug treatments, washed three times with TBS, and incubated with ice cold TD buffer at 4° C. for fifteen minutes. Cell extracts were scraped into 2 ml microcentrifuge tubes, subjected to mechanical disruption by 10 passages through a 23 gauge needle, and centrifuged at 16000×g for twenty minutes. The insoluble material was resuspended in 2 ml of 2× sample buffer (as described above) and the supernatant was diluted to 2 ml with 1 ml of 4× sample buffer. The two fractions were then subjected to 6% SDS-PAGE followed by immunoblot analysis.

Results

Detection of Hyperphosphorylated Pol II LS in Nuclear Speckles.

This experiment showed that, a subset of Pol II LS, which is detectable by the mAb H5, is localized in the nuclear speckles.

The intensity and pattern of intranuclear mAb H5 immunoreactivity fluctuates continuously during the cell cycle, while the level of mAb H5 binding to Pol II LS on immunoblots is constant. This indicates that the H5 epitope of Pol II LS is masked and unmasked as cells progress through the cell cycle. Consequently, unsynchronized cell nuclei are stained heterogeneously by mAb H5: most have a diffuse nucleoplasmic Pol II LS stained heterogeneously by mAb H5: most have a diffuse nucleoplasmic Pol II LS staining pattern. However, approximately 20% of the cells also have 20–50 discrete speckles, which co-localized with splicing protein SC35 and snRNP's of the pre-mRNA splicing class. In nuclei that have a speckled distribution of Pol II LS, the speckles are more easily visualized after the diffuse nucleoplasmic fraction of Pol II LS is extracted with nonionic detergent prior to fixation and mAb H5 immunostaining. Also, growth factors induce a rapid "burst" of intranuclear mAb H5 immunoreactivity. When serum starved cells are exposed to serum or purified growth factors, intense mAb H5 immunoreactivity appears in speckles and in the nucleoplasm surrounding the speckles. Taken together, the above results show that Pol II LS is detected in the speckles using mAb H5 under certain conditions.

A commercially available anti-Pol II LS mAb, ARNA3 (Krämer et al., *Molec. Gen. Genet.* 180: 193–199 (1980)), detects Pol II LS in the diffuse nucleoplasmic compartment, but it does not stain speckles. Another anti-Pol II LS antibody (8WG16) stains the diffuse nucleoplasmic compartment, but not in the speckles.

These immunostaining experiments show that Pol II LS in the diffuse nucleoplasm is detected by all anti-Pol II LS mAbs tested, but Pol II LS in the speckles of untreated cells is detected only by mAb H5.

Pol II LS in the diffuse nucleoplasm does not co-localize with SC35, which is distributed in a distinctive speckled pattern. However, diffusely distributed Pol II LS is readily extracted from the nucleus by Triton X-100™ surfactant (1% v/v), leaving an insoluble fraction of Pol II LS, which co-localizes with SC35. Immunoelectron microscopic studies show intense mAb H5 labeling in discrete clusters that are closely associated with ICG cluster.

The presence of Pol II LS in the Triton X-100™ surfactant insoluble residue was confirmed by solubilizing the residue, immunoprecipitating Pol II LS with mAb H5, and immunoblotting the precipitated protein with mAbs H5, H14 and SWG16. Pol II LS located in the speckles is tightly associated with an underlying nuclear structure, as indicated by its resistance to extraction by sodium deoxycholate. Speckle-bound Pol II LS is not released by nuclease/high salt extraction protocols, similar to speckle-bound SC35. In contrast to the speckle bound fraction of Pol II LS, the diffuse fraction is easily released by nonionic detergents and nuclease/salt extraction protocols.

The above results show that there are two populations of Pol II LS, which can be distinguished by differences in their intranuclear distribution, detergent solubility properties and accessibility to antibodies.

Monoclonal antibodies HS and H14 detect Pol II LS located in enlarged nuclear speckles in α-amanitin treated cells Alpha-amanitin, a compound that completely blocks Pol II-mediated transcription (Lindell et al., *Science* 170: 447–449 (1970)), induces a striking accumulation of SC35 in multiple intranuclear dots, which lack apparent interconnections (O'Keefe et al, *J. Cell Biol.*, 124: 249–260 (1994)). To distinguish the dot-like structures in transcriptionally inhibited cells from the speckle domains in transcriptionally active control cells, the former are referred to as "enlarged speckle domains," and the latter are referred to as "interconnected speckle domains."

This experiment was performed to determine whether Pol II LS redistributes with SC35 to the enlarged nuclear speckles in response to α-amanitin.

The results show that SC35 is distributed in speckles that appear to be interconnected or partially fused in control cell nuclei prepared by either protocol. Alpha-amanitin induces SC35 to redistribute to enlarged speckles lacking interconnections.

Pol II LS located in the enlarged speckles of α-amanitin treated cells is not detected by anti-Pol II mAb ARNA3 or mAb 8WG16. Finally, no significant change in the intranuclear distribution of hnRNP A1 was detected in α-amanitin treated cells.

The above results show that one anti-Pol II LS mAb (H5) stains speckles in untreated cells, and two anti-Pol II LS mabs (H5 and H14) stain the enlarged speckles in transcriptionally inhibited cells. Each mAb binds exclusively to Pol II LS on immunoblots and immunoprecipitations prepared from control and transcriptionally inhibited cells. Furthermore, mAbs H5 and H14 bind to different epitopes on the Pol II LS molecule.

mAbs H5, H14 and 8WG16 bind to different phosphorylated forms of Pol II LS

All known phosphorylation sites on Pol II LS have been mapped to the C-terminal domain (CTD), which is compromised of 52 tandem heptapeptide repeats similar or identical to the sequence Tyr-Ser-Pro-Thr-Ser-Pro-Ser, Sequence ID. NO: 1 (see, Corden et al., *Trends Biochem Sci.* 15: 383–387 (1990)). Some heptapeptide repeats vary from the consensus sequence (YSPTSPS), Sequence ID. NO: 1, by one, two or three amino acid residues, such as, for example, YSPTSPA, Sequence ID. NO: 2, or YSPTSPG, Sequence ID. NO: 3. Two major phosphorylated forms of Pol II LS have been defined in mammalian cells: Pol II0 is hyperphosphorylated predominantly on Ser and Thr residues in the CTD and is recognized by a SDS-PAGE mobility of approximately 240 kDa; Pol IIA is hypophosphorylated, and it migrates at approximately 220 kDa (Dahmus, M. E., *J. Biol. Chem.* 256: 3332–3339 (1981)).

Each mAb used in this study reacted differently to Pol II0, Pol IIA and the multiple intermediate forms of Pol II LS. MAb H14 binds well to Pol II0, Pol IIA and multiple intermediately phosphorylated forms in whole cell extracts. To show that MAb H14 binds to Pol II LS molecules that are phosphorylated to different degrees, Pol II LS was immunoprecipitated with mAb H14 and then treated with buffer, alkaline phosphatase, or alkaline phosphatase plus β-glycerophosphate prior to solubilization is SDS sample buffer. The three samples were subjected to PAGE and immunoblotted with mAb H14. MAb H14 bound to a series of bands (i.e. a smear) ranging from approximately 220 kDa to approximately 240 kDa in the untreated sample. However, mAb H14 bound only to an approximately 220 kDa band in the alkaline phosphatase treated sample. The alkaline phosphatase induced reduction of Pol II LS's electrophoretic mobility is completed blocked by β-glycerophosphate, a Ser/Thr phosphatase inhibitor. The binding of mAb H14 to Pol II LS can be completely abolished by pre-incubation of the immunoprecipitates with a greater concentration of alkaline phosphatase, indicating that the mAb H14 epitope is phosphorylation sensitive. MAb H5 did not bind to hypophosphorylated forms of Pol II LS, but it did bind strongly to a sharp band at approximately 240 kDa, i.e. Pol II0. Furthermore, the binding of mAb H5 to Pol II LS could also be abolished by alkaline phosphatase.

Speckle bound Pol II LS is hyperphosphorylated on C-terminal domain (CTD)

MAb H5 binds exclusively to Pol II0, and can therefore be used to localize this hyperphosphorylated form of Pol II LS in the cell nucleus. A fraction of Pol II0 distributes to the speckles, because mAb H5 stains these domains. Immunolocalization experiments showed that the speckle fraction of Pol II LS was highly resistant to Triton X-100™ surfactant extraction, whereas the diffusely distributed fraction of Pol II LS is readily extracted. These observations indicate that the predominant form of Pol II LS, which is bound tightly to the speckles, is hyperphosphorylated on the CTD.

Pol IIO is the predominant Pol II species in elongating transcription complexes in vitro and in vivo. Therefore, it is important to determine whether Pol II LS's transcription-dependent intranuclear redistribution correlates with altered phosphorylation of Pol II LS's CTD. Exposure of cells in 100 μM DRB for three hours induces Pol II LS to redistribute to enlarged speckles. Coincident with this redistribution, a substantial fraction of the total Pol II LS is dephosphorylated in vivo. This result is in agreement with previous studies showing that DRB is a CTD kinase inhibitor in vitro and in vivo. Significantly, the hypophosphorylated Pol II LS molecules are completely soluble in TD buffer. The dephosphorylation of Pol II LS is also reflected by diminished mAb H5 binding to Pol IIOin the supernatant fraction.

The above results show that DRB induces dephosphorylation of the CTD in a fraction of Pol II LS molecules. Simultaneously, mAb H5 immunostaining disappears from the diffuse compartment and intensifies in the enlarged speckle domains.

MAb H5, which binds specifically to Pol-IIO, immunostains the fraction of Pol II LS that is located in the enlarged round speckles of DRB treated cells. In addition, mAb H5 does not immunostain the diffuse nucleoplasm of fixed and permeabilized, DRB-treated cells. The biochemical data also suggest that Pol II LS molecules located in the enlarged speckle domains of DRB treated cells are hyperphosphorylated on the CTD (i.e. Pol IIO). A fraction of Pol IIO resists extraction in TD buffer, whereas Pol IIA and intermediate hypophosphorylated forms of Pol II LS are readily extracted with TD buffer. These data suggest that DRB induces dephosphorylation of Pol II LS in the diffuse nucleoplasmic compartment, and that it independently induces the detergent insoluble fraction of Pol IIO to redistribute from an interconnected speckled pattern to an enlarged speckled pattern. To further test the hypothesis that Pol IIO is redistributed to enlarge speckled domains in transcriptionally inhibited cells, α-amanitin-treated cells were subjected to the TD fractionation procedure. In contrast to DRB, α-amanitin did not induce a change in Pol II LS's electrophoretic mobility. Thus, Pol II LS extracted from α-amanitin treated cells has an electrophoretic mobility that is similar to control cells. The ratio of Pol IIO to partially dephosphorylated forms is similar in α-amanitin treated and control cells, and there is very little Pol IIA. These results reflect the fact that α-amanitin and DRB inhibit Pol II-mediated transcription by different mechanisms. When α-amanitin treated cells are extracted in TD buffer, Pol IIO fractionates with the residue and the less phosphorylated forms of Pol II LS are soluble.

These experiments show that in control, DRB and α-amanitin treated cells, the TD pellet contains exclusively Pol IIO, whereas the TD supernatant contains multiple phosphorylated forms of Pol II LS. The TD extracted nuclear residues of α-amanitin treated cells were also immunostained with mAb H5, confirming that Pol IIO is distributed in a speckled pattern lacking interconnections.

Therefore, the predominant form of Pol II LS, which is bound to the speckles in the cell nucleus, is hyperphosphorylated on the C-terminal domain and is detected by the monoclonal antibody H5.

Modifications and variations of the present invention, anti-Pol II LS antibodies and methods of use thereof and a method for molecule delivery to the cell nucleus will be obvious to those skilled in the art from the foregoing detailed description. Such modifications and variations are intended to come within the scope of the appended claims.

I claim:

1. A method for delivering a molecule to a cell nucleus comprising conjugating the molecule to a macromolecule comprising the C-terminal domain of a large subunit of RNA polymerase II, and introducing the conjugate directly to the cell.

2. The method of claim 1 wherein the molecule is a pharmaceutical agent.

3. The method of claim 1 wherein the molecule is delivered to an RNA-Polymerase II-mediated transcription site in the nucleus.

4. A conjugate comprising a portion of the large subunit of RNA polymerase II consisting of the C-terminal domain of the large subunit of RNA polymerase II conjugated to a macromolecule selected from the group consisting of an oligonucleotide, a protein, and a pharmaceutical agent.

5. The conjugate of claim 4 further comprising a pharmaceutically acceptable carrier for use in delivering a molecule to a cell.

6. The conjugate of claim 4 wherein the oligonucleotide is a ribozyme.

7. The method of claim 1 wherein the molecule is selected from the group consisting of oligonucleotides and proteins.

8. The conjugate of claim 4 wherein the macromolecule is an oligonucleotide or a pharmaceutical agent.

9. A composition comprising the conjugate of claim 4 and a cell.

* * * * *